(12) United States Patent
Felder et al.

(10) Patent No.: US 9,381,054 B2
(45) Date of Patent: Jul. 5, 2016

(54) SELF HOLDING FEATURE FOR A SCREW

(71) Applicant: DEPUY SYNTHES PRODUCTS, INC., Raynham, MA (US)

(72) Inventors: Martin Felder, Solothurn (CH); Oliviero Durante, Solothurn (CH)

(73) Assignee: DePuy Synthes Products, Inc., Raynham, MA (US)

( * ) Notice: Subject to any disclaimer, the term of this patent is extended or adjusted under 35 U.S.C. 154(b) by 74 days.

(21) Appl. No.: 13/689,875

(22) Filed: Nov. 30, 2012

(65) Prior Publication Data

US 2013/0144345 A1    Jun. 6, 2013

Related U.S. Application Data

(60) Provisional application No. 61/567,390, filed on Dec. 6, 2011.

(51) Int. Cl.
  *A61B 17/84*  (2006.01)
  *A61B 17/88*  (2006.01)
  *A61B 17/86*  (2006.01)
  *A61B 17/74*  (2006.01)

(52) U.S. Cl.
  CPC ........... *A61B 17/844* (2013.01); *A61B 17/8605* (2013.01); *A61B 17/8875* (2013.01); *A61B 17/74* (2013.01); *A61B 17/864* (2013.01); *A61B 17/8615* (2013.01); *A61B 17/888* (2013.01)

(58) Field of Classification Search
  CPC .. A61B 17/84; A61B 17/844; A61B 17/8605; A61B 17/8615; A61B 17/864; A61B 2017/8655

USPC ............................ 606/60, 246–279, 300–331
  See application file for complete search history.

(56) References Cited

U.S. PATENT DOCUMENTS

| | | | |
|---|---|---|---|
| 5,484,440 A | 1/1996 | Allard | |
| 6,423,067 B1 | 7/2002 | Eisermann | |
| 6,554,834 B1 | 4/2003 | Crozet et al. | |
| 6,620,167 B2 * | 9/2003 | Deslauriers et al. | 606/308 |
| 7,914,561 B2 * | 3/2011 | Konieczynski et al. | 606/280 |
| 8,216,243 B2 | 7/2012 | Yevmenenko et al. | |
| 2003/0074003 A1 | 4/2003 | Deslauriers et al. | |
| 2006/0264936 A1 * | 11/2006 | Partin et al. | 606/61 |
| 2010/0145388 A1 * | 6/2010 | Winslow et al. | 606/264 |
| 2011/0270322 A1 | 11/2011 | Olsen et al. | |

FOREIGN PATENT DOCUMENTS

| | | |
|---|---|---|
| CN | 101304699 A | 11/2008 |
| DE | 3119583 A1 | 12/1982 |
| EP | 1 090 595 | 4/2001 |
| EP | 1 561 429 | 8/2005 |
| WO | WO 98/27883 A1 | 7/1998 |
| WO | 99/11177 | 3/1999 |

* cited by examiner

*Primary Examiner* — Christopher Beccia
(74) *Attorney, Agent, or Firm* — Wayne C. Jaeschke, Jr.

(57) ABSTRACT

A bone fixation device comprises an elongated body extending from a head at a proximal end to a shaft at a distal end along a central longitudinal axis. A slotted opening extends distally into the head by a predetermined distance, the opening defining a spring portion on a lateral side thereof, the spring portion being biased toward the central longitudinal axis and configured to be deflectable away from the central longitudinal axis upon application of a radially expansive force thereto.

8 Claims, 5 Drawing Sheets

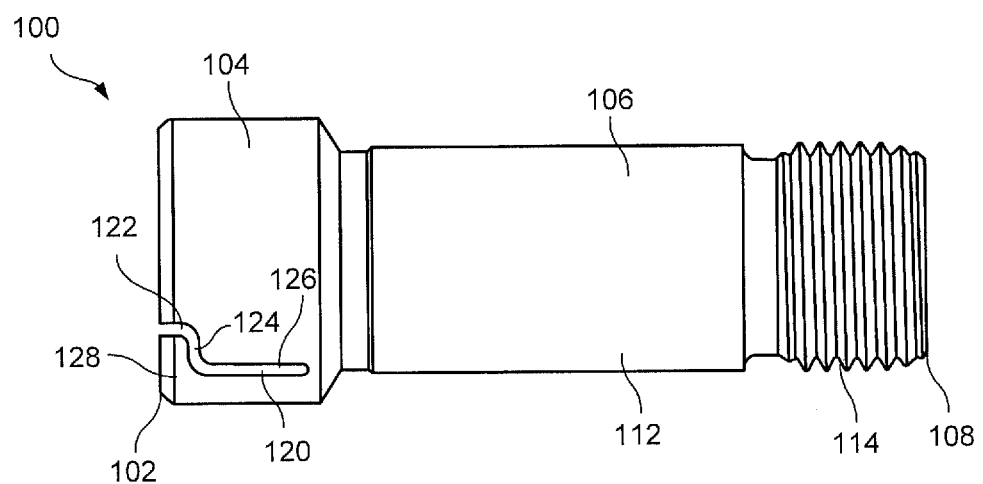
F I G. 4

SELF HOLDING FEATURE FOR A SCREW

PRIORITY CLAIM

The present application claims priority to U.S. Provision Application Ser. No. 61/567,390 entitled "Self Holding Feature for a Screw" filed on Dec. 6, 2011, the entire disclosure of which is incorporated herein by reference.

BACKGROUND INFORMATION

Fractures of long bones (e.g., the femur) commonly occur in a neck of the bone, an intertrochanteric region or in a peritrochanteric region. Such fractures are often fixed through the insertion of an intramedullary device (e.g., an intramedullary nail) into a medullary cavity of the bone. A trochanteric fixation implant (e.g., a bone screw) may then be inserted laterally through the intramedullary device transverse to a longitudinal axis of the bone to pass into a head of the bone. Trochanteric fixation implants are often guided into the bone and through the intramedullary device via a screwdriver. However, the screwdriver is prone to disengagement from a head of the trochanteric fixation implant during insertion, thus increasing the time necessary to complete a bone fixation procedure and causing other complications.

SUMMARY OF THE INVENTION

The present invention is directed to a bone fixation device comprising an elongated body extending from a head at a proximal end to a shaft at a distal end along a central longitudinal axis. A slotted opening extends distally into the head by a predetermined distance, the opening defining a spring portion on a lateral side thereof, the spring portion being biased toward the central longitudinal axis and configured to be deflectable away from the central longitudinal axis upon application of a radially expansive force thereto.

BRIEF DESCRIPTION OF THE DRAWINGS

FIG. 4 shows a second perspective view of the bone fixation element of FIG. 1;

DETAILED DESCRIPTION

Figure 1:
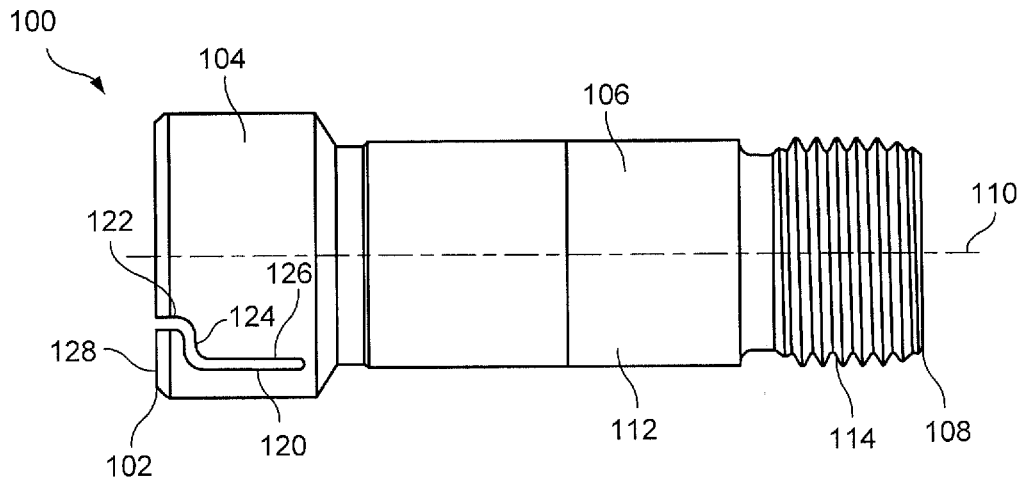
FIG. 1 shows a first perspective view of a exemplary bone fixation element according to the present invention.
Figure 2:
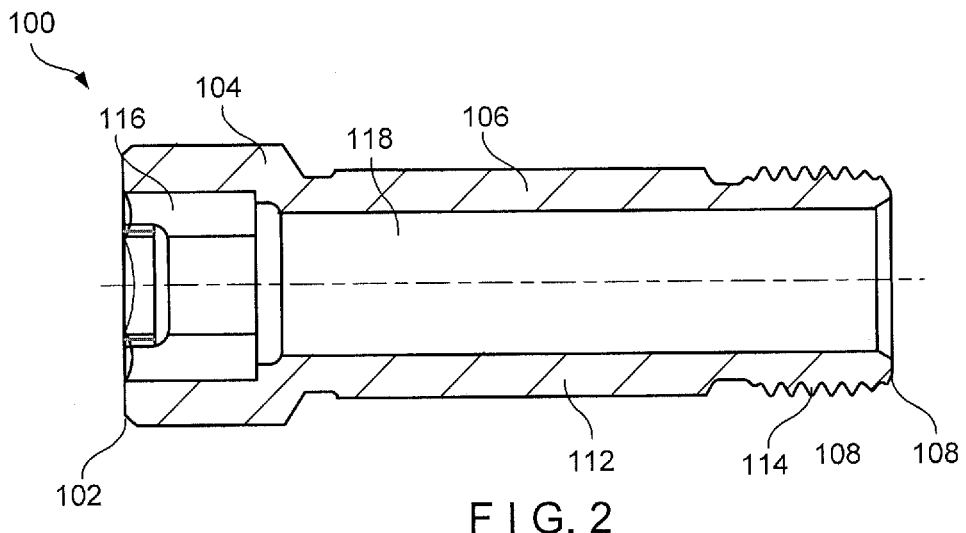
FIG. 2 shows a partial cross-sectional view of the bone fixation element of FIG. 1.

The present invention may be further understood with reference to the following description and the appended drawings, wherein like elements are referred to with the same reference numerals. The present invention relates generally to devices and methods for the fixation of a fractured or otherwise damaged bone. Specifically, the present invention relates to methods and devices for inserting a bone fixation element into a bone temporarily lockingly engaging a driving mechanism to retain a position thereof against the bone fixation element. The exemplary bone fixation element according to the invention includes a head and an elongated shaft extending distally therefrom. The head comprises a spring mechanism biased radially inward into a recess configured to receive a distal end of the driving mechanism. The exemplary driving mechanism according to the invention is formed with a substantially spherical distal end. Upon insertion of the spherical distal end into the recess, the spring is moved radially outward, a bias of the spring applying a force to the spherical distal end to lock the bone fixation element to the driving mechanism. By lockingly engaging the driving mechanism during insertion, loosening of the bone fixation element relative to the driving mechanism is minimized, thus reducing the time and effort necessary to securely seat the bone fixation element in a target position in the bone. It is noted that although the exemplary system and method are discussed with respect to a trochanteric fixation screw for use in a femur, the invention may be used in any other bone fixation procedure in any other bone of the body by modifying the dimensions and shape of the apparatus to suit the particular anatomy. The term "proximal" as used herein refers to a direction approaching a physician or other use while the term "distal" refers to a direction approaching a target fixation site of a bone.

As shown in FIGS. 1-4, a bone fixation element 100 (e.g., a bone screw) according to an exemplary embodiment of the invention extends along a central longitudinal axis 110 from a proximal end 102 comprising a head 104 to a shaft 106 terminating at a distal end 108. The bone fixation element 100 has a substantially circular cross-sectional shape with an outer diameter of the head 104 greater than an outer diameter of the shaft 106 so that the head 104 may seat against a structure defining a limit to which the shaft 106 may be inserted through the structure. The shaft 106 according to this embodiment comprises a first substantially smooth portion 112 and a second threaded portion 114 distal thereof. As those skilled in the art will understand, the first portion 112 may be configured to engage a trochanteric channel (not shown) extending through an intramedullary nail (not shown) while the second portion 114 is configured to threadedly engage the bone in the trochanter (not shown). However, as would be understood by those skilled in the art, any portion of the shaft 106 may be threaded or unthreaded to conform to the requirements of a particular procedure. Furthermore, although the first and second portions 112, 114 of the shaft 106 are depicted as having two different diameters, any relative dimensions may be selected to conform to the requirements of a particular procedure without deviating from the scope of the invention.

The head 104 comprises a recess 116 extending distally thereinto from the proximal end 102 by a predetermined distance selected to conform to a dimension of a distal end of a driving mechanism 200, as will be described in greater detail later on. The recess 116 may be aligned with the central longitudinal axis 110 and may have a substantially hexagonal cross-sectional shape in a plane perpendicular to the longitudinal axis of the bone fixation element 100. It is noted, however, that any other cross-sectional shape may be used for the recess 116 without deviating from the scope of the invention (e.g., slotted, square, torx, etc.) so long as the shape cooperates with a shape of an end of a driving mechanism to non-rotatably couple a driving mechanism inserted into the recess 116 to the bone fixation element 100.

Figure 3:
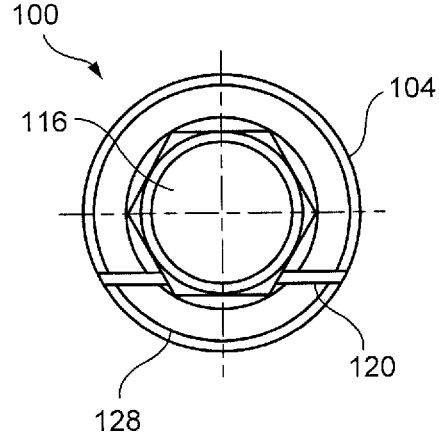
FIG. 3 shows a perspective view of the bone fixation element of FIG. 1 from a proximal direction.

In the exemplary embodiment of FIGS. 1-4, the recess 116 extends completely through the head 104 and is open to a channel 118 extending longitudinally through the shaft 106. A slot 120 extends into the head 104 from the proximal end 102 forming a chord in a proximal face of the head 104 as shown in FIG. 3. The slot 120 extends completely through outer walls of the head 104. The slot 120 may be provided in any configuration along the head 104 so long as the slot 120 permits a portion of a wall of the head 104 to flex outward as a driving mechanism is inserted into the recess 116 and then snap back under a natural bias to temporarily lock the driving mechanism within the recess 116 as will be described in more detail below. In this embodiment, the slot 120 penetrates the wall of the head 104 into the recess 116 as shown in FIG. 3. The slot 120 is formed as an elongated cut with a first slot portion 122 extending in a plane substantially parallel to the longitudinal axis 110, a second slot portion 124 extending in a plane substantially perpendicular to the longitudinal axis 110 outward from the axis 110 and a third slot portion 126 extending in a plane substantially parallel to the longitudinal axis 110. The slot 120 defines a spring portion 128 on a lateral side thereof. Interfaces between the first, second and third slot portions 122, 124, 126 are substantially rounded with a predetermined radius of curvature selected to increase a deflectability of the spring portion 128 away from the central longitudinal axis 110, as will be described in greater detail later on. A length of the second slot portion 124 is selected to permit a predetermined deflection of the spring portion 128 away from the central longitudinal axis 110 while preserving a biasing force urging the spring portion 128 back toward the longitudinal axis 110.

Figure 5:
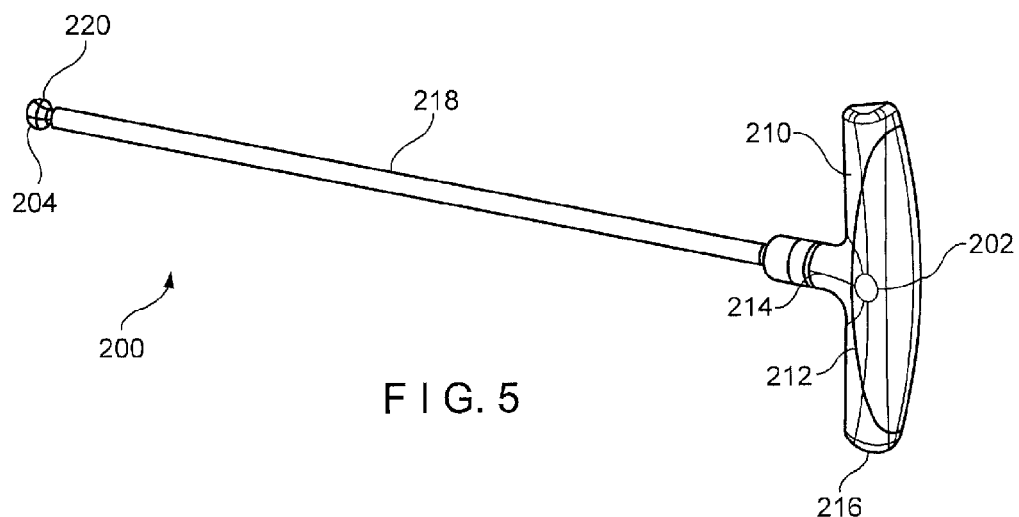
FIG. 5 shows a first perspective view of a driving mechanism according to the invention.
Figure 6:
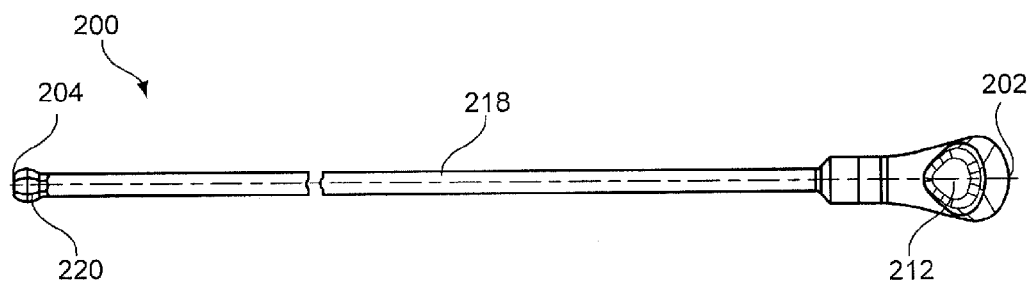
FIG. 6 shows a second perspective view of the driving mechanism of FIG. 5.

FIGS. 5-6 depict an exemplary driving mechanism 200 according to the invention. The driving mechanism 200 extends from a proximal end 202 to a distal end 204 along a central longitudinal axis 206. A handle 208 is provided at the proximal end 202, the handle 208 comprising first and second arms 210, 212 extending substantially perpendicular to the longitudinal axis 206. It is noted, however, that the handle 208 may be formed in any other shape without deviating from the scope of the invention. The first and second arms 210, 212 are permanently connected (e.g., via laser welding, bonding, etc.) to an elongated element 214 extending along the longitudinal axis 206. The handle 208 may further be provided with a silicone overmold 216. A shaft 218 extends distally from the elongated element 214 and comprises a tip 220 at a distal end thereof. The tip 220 is formed with a substantially spherical shape defined by a plurality of faceted walls configured to engage the hexagonal walls of the recess 116. Specifically, the tip 220 may comprise six facets configured to converge at proximal and distal ends of the tip 220, forming the spherical shape. Engagement of the faceted walls with the bone fixation element 100 couples the driver to the bone fixation element non-rotatably with respect to the longitudinal axis of the bone fixation element 100 while the substantially spherical shape permits limited pivot movement of the driving mechanism relative to the bone fixation element 100 about an axis substantially perpendicular to the longitudinal axis of the bone fixation element 100. A length of the shaft 218 is selected to conform to the requirements of a target procedure and a diameter of the tip 220 conforms to the dimensions of the recess 116. For example, a tip 220 according to this embodiment may be approximately 8 mm in diameter while a diameter of the recess is substantially similar. An elongated channel 222 extends through the driving mechanism 200 from the proximal end 202 to the distal end 204 (e.g., to permit insertion of bone cement, etc. into the bone). In another embodiment, the tip 220 may be provided with any number of facets extending circumferentially about the substantially spherical tip 220 to conform to a corresponding number of facets in the recess 116.

Figure 7:
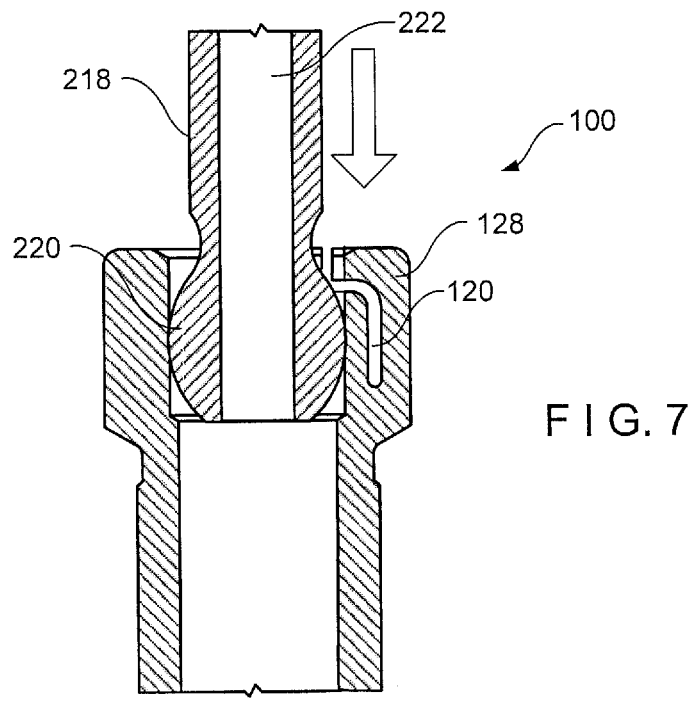
FIG. 7 shows the bone fixation element of FIG. 1 in a first operative configuration.
Figure 8:
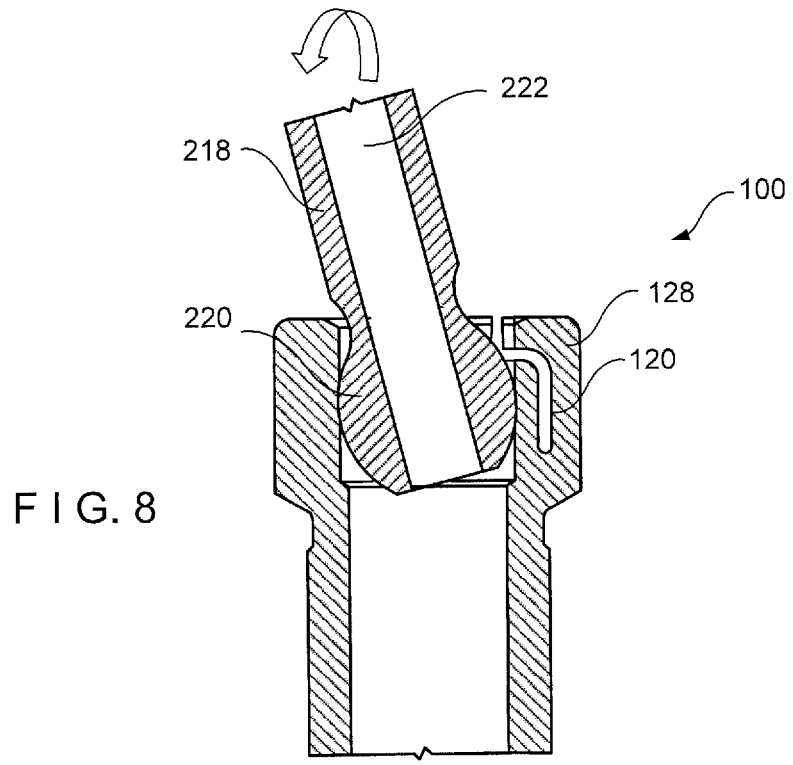
FIG. 8 shows the bone fixation element of FIG. 1 in a second operative configuration.

In accordance with an exemplary method according to the invention, as shown in FIGS. 7-8, the tip 220 is inserted into the recess 116, the insertion causing the spring portion 128 to flex radially outward to permit movement of the tip 220 completely into the recess 116. Once the tip 220 has moved into the recess 116, the spring portion 128 returns to a biased configuration substantially in longitudinal alignment with the central longitudinal axis 110 to lock a position of the tip 122 in the recess 116. As those skilled in the art will understand, by applying a spring retention force to the tip 220, a physician or other user may pivot the driving mechanism 200 at a variety of angles with respect to the central longitudinal axis 110 of the bone fixation element 100 without causing a subsequent pivotal movement of the bone fixation element 100 to aid in insertion thereof, as those skilled in the art will understand. In an exemplary embodiment, the biasing force applied to the tip 222 by the spring portion 128 is sufficient to prevent rotation of the tip 222 within the recess 116. The driving mechanism 200 is then used to screw the bone fixation element 100 into the bone in a target position. To separate the tip 222 from the recess 116, a physician or other user pivots the driving mechanism 200 at a predetermined angle relative to the bone fixation element 100, the pivotal movement causing the tip 220 to become separated from the bone fixation element 100.

Figure 9:
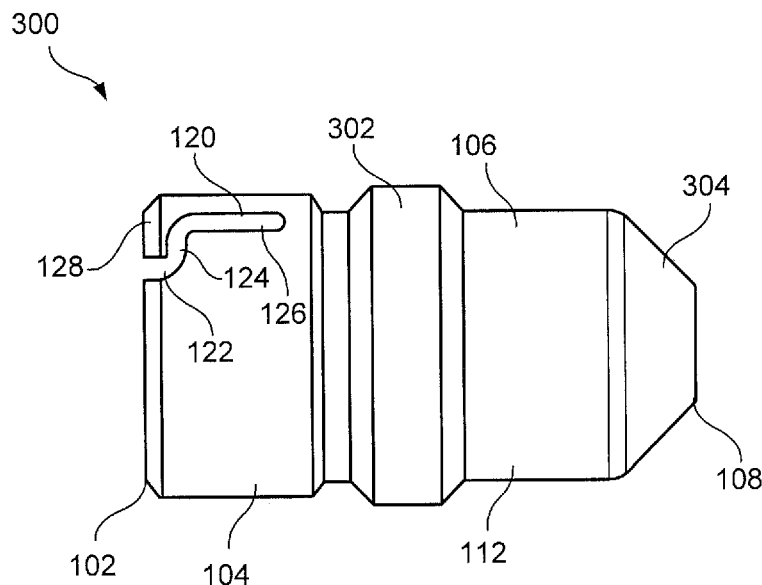
FIG. 9 shows a perspective view of a bone fixation element according to a first alternate embodiment of the invention.

FIG. 9 depicts a bone fixation implant 300 according to a first alternate embodiment of the invention, the bone fixation implant 300 being formed substantially similar to the bone fixation implant 100, wherein like elements have been referenced with like reference numerals. Specifically, the shaft 106 of the bone fixation implant 300 is non-threaded and comprises a circumferential abutment 302 extending radially thereoutof by a predetermined distance. In an exemplary embodiment, the abutment 302 may be positioned along a proximal portion of the shaft 106 although any other position may be used without deviating from the scope of the invention. In an exemplary embodiment, the abutment 302 may be configured and dimensioned to frictionally engage an inner wall of a hole (not shown) extending through a bone fixation element (e.g., a bone plate, an intramedullary nail, etc.) or a bone, as those skilled in the art will understand. A distal portion of the bone fixation implant 300 may be provided with a tapered wall 304 reducing a diameter of the distal end 108 to, for example, aid in insertion thereof into the bone fixation element or bone, as those skilled in the art will understand. Furthermore, it is noted that although the bone fixation implant 300 is depicted as being unthreaded, any portion of the shaft 106 may be provided with threading without deviating from the scope of the invention.

Figure 10:
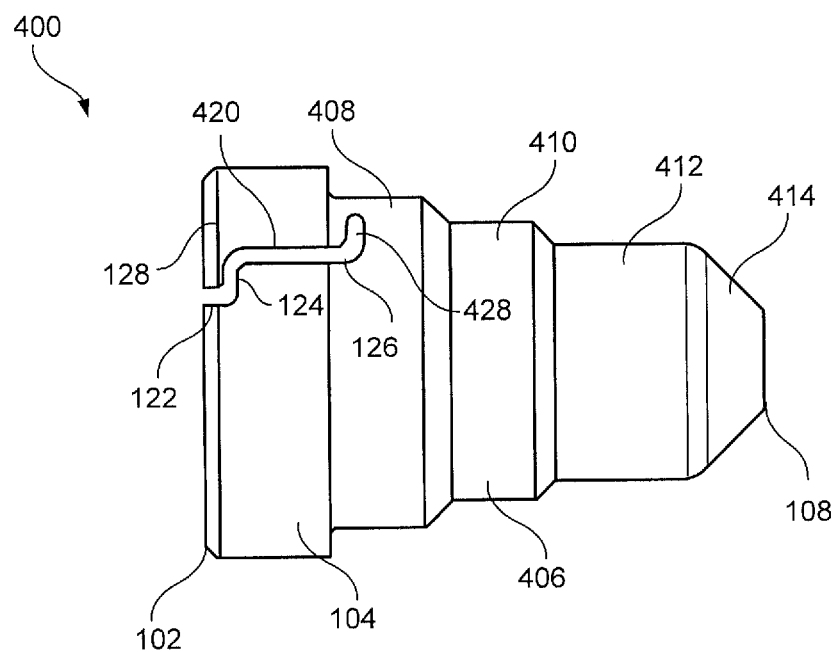
FIG. 10 shows a perspective view of a bone fixation element according to a second alternate embodiment of the invention.

FIG. 10 depicts a bone fixation implant 400 according to a second alternate embodiment of the invention, the bone fixation implant 400 being formed substantially similar to the bone fixation implant 100, wherein like elements have been referenced with like reference numerals. A shaft 406 of the bone fixation implant 400 is non-threaded and is formed with a substantially tapered shape. Specifically, the shaft 406 comprises first, second and third sections 408, 410, 412 each having a smaller diameter than the last. A further tapered portion 414 is provided at a distal end of the third section 412, the tapered portion 414 tapering down in diameter toward the distal end 108. The bone fixation implant 400 also varies from the bone fixation implant 100 in a configuration of a slot 420 provided thereon. Specifically, in addition to the first, second and third slot portions 122, 124, 126, the slot 420 also comprises a fourth slot portion 428 extending at an angle to the longitudinal axis 110. In an exemplary embodiment, the fourth slot portion 428 may extend orthogonally to the longitudinal axis 110 although any other angle may be used without deviating from the scope of the invention. As those skilled in the art will understand, the fourth slot portion 428 serves to increase a deflectability of the spring portion 128.

It will be apparent to those skilled in the art that various other modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A bone fixation device comprising:
    an elongated body having a proximal end having a head portion and a distal end, the elongated body extending from the proximal end of the head to a shaft at the distal end along a central longitudinal axis, wherein the head portion has a larger diameter than the shaft portion and the head portion is adapted to seat against a structure to define a limit to which the shaft may be inserted through the structure;
    a slotted opening extending distally from the proximal end into the head by a predetermined distance, the opening defining a spring portion on a lateral side thereof, the spring portion being biased toward the central longitudinal axis and configured to be deflectable away from the central longitudinal axis upon application of a radially expansive force thereto; and
    a recess extending distally into the head from the proximal end, the recess being configured and dimensioned to engage a driving mechanism and to permit the driving mechanism to pivot with respect to the central longitudinal axis of the bone fixation device without causing pivotal movement of the bone fixation device, wherein the driving mechanism comprises a shaft having a substantially spherical tip at a distal end thereof, and the substantially spherical tip comprises a plurality of circumferentially disposed facets.

2. The bone fixation device of claim 1, wherein the recess is aligned with the central longitudinal axis.

3. The bone fixation device of claim 1, wherein the slotted opening is separated from the recess.

4. The bone fixation device of claim 1, wherein a shape of the recess is one of hexagonal, slotted, square and torx-shaped.

5. The bone fixation device of claim 1, wherein the slotted opening extends substantially parallel to the central longitudinal axis.

6. The bone fixation device of claim 1, wherein a first portion of the slotted opening extends at an angle to the central longitudinal axis, the first portion being configured to increase a deflectability of the spring portion.

7. The bone fixation device of claim 6, wherein the first portion is located at a distal end of the slotted opening.

8. The bone fixation device of claim 1, wherein a portion of the shaft is threaded.

* * * * *